United States Patent [19]

Ando et al.

[11] Patent Number: 5,064,599
[45] Date of Patent: Nov. 12, 1991

[54] PROCESS FOR PRODUCING AN ANTIBACTERIAL FIBER ARTICLE

[75] Inventors: Satoshi Ando; Akira Dohno, both of Osaka; Zenji Hagiwara, Kusatsu, all of Japan

[73] Assignees: Kanebo Limited, Tokyo; Hagiwara Giken Limited, Shiga, both of Japan

[21] Appl. No.: 512,566

[22] Filed: Apr. 24, 1990

Related U.S. Application Data

[63] Continuation of Ser. No. 139,663, Dec. 30, 1987, abandoned.

[30] Foreign Application Priority Data

Jan. 8, 1987 [JP] Japan .................................. 62-1079

[51] Int. Cl.$^5$ ........................... D01F 8/04; D06C 7/00
[52] U.S. Cl. ................................ 264/237; 264/234; 264/257; 264/103; 264/171; 264/345; 162/157.2
[58] Field of Search ............... 264/171, 237, 234, 257, 264/103, 345; 162/157.2, 181.5

[56] References Cited

U.S. PATENT DOCUMENTS

| | | | |
|---|---|---|---|
| 3,998,988 | 12/1976 | Shimomai et al. ................... | 428/373 |
| 4,115,130 | 9/1978 | Crump et al. ....................... | 428/907 |
| 4,525,410 | 6/1985 | Hagiwara et al. ................... | 428/241 |
| 4,627,950 | 12/1986 | Matsui et al. ...................... | 264/103 |
| 4,643,182 | 2/1987 | Klein ................................. | 428/290 |

FOREIGN PATENT DOCUMENTS

0116865  8/1984  European Pat. Off. .

OTHER PUBLICATIONS

Chemical Abstract #154643k, vol. 105, No. 18, Nov. 3, 1986, p. 80.
Chemical Abstract #231474c, vol. 101, No. 26, Dec. 24, 1984, p. 31.

*Primary Examiner*—Hubert C. Lorin
*Attorney, Agent, or Firm*—Nixon & Vanderhye

[57] ABSTRACT

Zeolite particles retaining antibacterial metal ion, such as Ag, Cu or Zn ion, at ion-exchangeable sites of the zeolite are included in a low-melting component of conjugated fibers which comprise a low-melting component and a high-melting component. Upon heating, the low-melting component spreads to cause more zeolite particles to be exposed, which yields higher antibacterial activity in a fiber article produced from the conjugated fibers.

13 Claims, No Drawings

PROCESS FOR PRODUCING AN ANTIBACTERIAL FIBER ARTICLE

This is a continuation of application Ser. No. 07/139,663, filed Dec. 30, 1987, now abandoned.

FIELD OF THE INVENTION

This invention relates to a fiber material suitable for producing an antibacterial fiber article such as nonwoven fabrics, and to an antibacterial fiber article produced therefrom.

BACKGROUND OF THE INVENTION

It has been known for a long time that some metal ions such as silver ion, copper ion, and zinc ion have antibacterial properties. For example, silver ion has been widely utilized as a disinfectant or a germicide in the form of a solution of silver nitrate. However, the use of silver nitrate as a solution is inconvenient for handling and further there is the disadvantage that such a solution can be used only for restricted purposes.

Then, a polymeric substance holding the metallic ions was proposed for use in various fields to reduce the aforementioned disadvantages. Many methods of incorporating the metal ions into a polymeric substance are known, for example, the method of binding or adding fine wires or powder of the metals themselves to a polymer and the method of incorporating compounds of the metals into a polymer.

However, in the methods in which the metals themselves are used as mentioned above, there is the disadvantage that the metals show poor compatibility with polymers because the specific weights and Young's moduli of metals are usually very high compared with those of conventional polymers. In addition, such metals lead to very expensive products, with heavy weights as they are necessarily used in a large amounts.

In the method wherein compounds of the metals are used, the products obtained can be utilized only for restricted purposes because of the great influence of the compounds on polymer properties, or else the product shows poor durability of antibacterial performance because the metal ions are merely contained in or attached to the polymer and, accordingly, they easily fall away from the polymer while being used.

For no or less disadvantages such as those mentioned above, a method was proposed wherein a polymer contains organic functional groups having an ion exchange function or a complex forming function and, in turn, these groups retain the metal ions (for example cf. DE-C-963 192). However, in this method, the adverse effect of these functional groups on physical properties of the polymer cannot be disregarded.

Whether the functional groups are chemically introduced into a polymer or compounds having the functional groups are added in a polymer, the type of polymers and the type and amount of functional groups capable of being used are limited to avoid noticeable changes in physical properties of polymers.

U.S. Pat. No. 4,115,130 and FR-A1 061 158 describe a biocidal composition suitable for use in marine antifouling coatings, which comprises a water-insoluble mineral having an internal pore structure, e.g. zeolites, which contains within the pores or is saturated with a biocidal compound effective against marine growth, e.g. metals, metal compounds or organo-metal compounds.

In U.S. Pat. No. 4,525,410, one of the present inventors and others proposed a particle-packed fiber article having antibacterial properties. Specific zeolite particles retaining therein a metal ion having a bactericidal activity are packed and retained in a mixed fiber assembly composed of low-melting thermoplastic synthetic fibers and ordinary fibers. The zeolite particles are retained by welding of the low-temperature thermoplastic synthetic fibers in a state of allowing the contact thereof with an external fluid.

In order to provide fiber articles having antibacterial properties, it has been known for a long time to after-treat the fiber articles with antibacterial agents or antifungous agents. However, such after-treatment fails to provide durable antibacterial effects.

One of the present inventors and others also proposed a polymer article having antibacterial properties comprising at least one organic polymer and zeolite articles contained in the polymer and retaining at least one metal ion having antibacterial properties at ionexchangeable sites of the zeolite (EP-B1-116, 865, and U.S. Pat. No. 4,775,585 filed Jan. 29, 1987). The illustrated polymer article has the shape of granules, films, fibers and so on. In the case of fibers, it is described that the zeolite may be contained in a sheath component of sheath-core conjugated fibers.

SUMMARY OF THE INVENTION

The object of the present invention is to enhance the antibacterial properties of a fiber article composed of fibers which contain zeolite particles retaining therein metal ion having antibacterial properties.

Another object of the invention is to yield a desired level of antibacterial properties with a less amount of such zeolite particles.

According to the invention, the above objects are attained by a fiber material for an antibacterial fiber article, characterized in that zeolite particles retaining therein at least one metal ion having antibacterial properties at ionexchangeable sites of the zeolite are retained in a low-melting component of conjugated fibers comprising said low-melting component and a high-melting component, provided that the low-melting component occupies at least a part of the periphery of the cross section of the fiber, and the zeolite particles have a specific surface area of at least 150 m$^2$/g and a SiO$_2$/Al$_2$O$_3$ ratio of at most 14.

When the fiber material of the invention is formed into a particular form of a fiber article and heated at temperatures above the melting point of the low-melting component of the conjugated fibers and below the melting point of the high-melting component to melt the low-melting component, the low-melting component spreads to increase its surface area. As a result, more zeolite particle retaining at least one metal ion having antibacterial properties at ion-exchangeable sites of the zeolite (hereinafter referred to as antibacterial zeolite) which are contained in the low-melting component come to exist on the surface of the fibers or in its vicinity, which results in an increased antibacterial effect and enhanced rapidity of the antibacterial effect. Further, the low-melting component which is thus melted and then cooled to solidify forms nodes at intersections of the fibers and functions to maintain the shape of the fiber article.

In the fiber material of the present invention, the low-melting component should be exposed in at least a part of the periphery of the cross section of the fibers.

Otherwise the low-melting component cannot spread to increase its surface area when melted.

DESCRIPTION OF THE PREFERRED EMBODIMENT

The cross section of the conjugated fibers may be, for instance, of a sheath-core structure composed of a core comprising the high-melting component and a sheath comprising the low-melting component, an incomplete sheath-core structure composed of a core comprising the low-melting component and a sheath comprising the high-melting component with the core being partially exposed at the periphery of the fiber cross section, or a side-by-side structure in which the low-melting component is placed side by side with the high-melting component. The periphery of the fibers need not be circular. The ratio of the area of the high-melting component to the area of the low-melting component in the fiber cross section may depend upon, for instance, the kind of the components used, the type of the fiber article for end use and configuration of the conjugation, but is preferably in a range of from 30:70 to 70:30 in general. These conjugated fibers may be produced by any known methods.

It is preferred in the invention that the difference between the melting point of the high-melting component and that of the low-melting component is at least 20° C., particularly at least 40 C. Any known organic polymers may be used as the components. For instance, the combination of the high-melting component and the low-melting component may be selected from the group consisting of polyester/polyester, polyester/polyolefine, polyester/polyamide, polyolefine/polyolefine and polyamide/polyamide. Specifically, examples of the high-melting polyester in the combination of polyester/polyester include usual polyethylene terephthalate, polyhexamethylene terephthalate, polytetramethylene terephthalate, poly-1,4-dimethyl-cyclohexane terephthalate and polypivalolactone. Examples of the low-melting polyester include copolyesters composed of predetermined amounts of aliphatic dicarboxylic acids such as adipic acid and sebacic acid, aromatic dicarboxylic acids such as phthalic acid, isophthalic acid and naphthalene dicarboxylic acid and/or alicyclic dicarboxylic acids such as hexahydroterephthalic acid and hexahydroisophthalic acid, and aliphatic or alicyclic diols such as diethylene glycol, polyethylene glycol, propylene glycol and p-xylilene glycol, if desired, with the addition of oxy acids such as p-hydroxybenzoic acid. There may be illustrated a copolyester obtained from terephthalic acid and ethylene glycol with the addition of isophthalic acid and 1,6-hexanediol.

In the combination of polyester/polyolefine, the high-melting polyester may be those described above. Examples of the low-melting component, polyolefine, include polyethylene, ethylene-vinyl acetate copolymer (hereinafter referred to as EVA), saponification products thereof, ethylene-propylene copolymer and mixtures of polypropylene and EVA.

As the polyamide in the combination of polyester/polyamide may be named nylon 6, nylon 66, nylon 12 or copolymers thereof.

As the high-melting component in the combination of polyolefine/polyolefine may be named polypropylene or copolymers composed mainly of propylene. As the low-melting component may be named the aforesaid polyethylene, EVA, saponification products thereof, ethylene-propylene copolymer, and mixtures of polypropylene and EVA.

As the high-melting polyamide in the combination of polyamide/polyamide may be named nylon 6, nylon 66 and nylon 12, and as the low-melting polyamide may be named copolymers, terpolymers or, mixtures thereof.

Of course, components other than these illustrated above may also be used. In the case of the incomplete sheath-core type, the low-melting component preferably has a lower melting point and a lower fluid viscosity so that it can easily spread upon melted. Therefore, polyolefine and polyamide are preferred as the low-melting component rather than polyester.

The fibers may contain components other than metal-zeolite, such as polymerization catalysts, stabilizers, delustering agents, optical whitening agents, organic or inorganic pigments, inorganic fillers and various plasticisers.

As the antibacterial zeolite particles, the zeolite particles disclosed in U.S. Pat. No. 4,525,410, EP-B1-116,865 and the U.S. Pat. No. 4,775,585 filed Jan. 29, 1987, may be used. Thus, the antibacterial zeolite particles to be used in this invention are natural or synthetic zeolite particles composed of aluminosilicate retaining one or more metal ions having antibacterial properties at the ion-exhangeable sites thereof. Preferred examples of metal ions having antibacterial properties are ions of Ag, Cu, Zn, Fe, Cr, Ni, Sn and Hg. Among these, Ag, Cu, Zn, particularly Ag, are preferred.

These antibacterial metals can be used solely or as a mixture thereof.

Zeolites are generally aluminosilicates having a three-dimensional skeleton structure and are generally represented by the formula $xM_{2/n}O.Al_2O_3.ySiO_2.zH_2O$, written with $Al_2O_3$ as a basis, wherein M represents an ion-exchangeable metal ion, which is usually the ion of a monovalent or divalent metal; n corresponds to the valence of the metal; x is a coefficient of the metal oxide; y is a coefficient of silica; and z is the number of molecules of water of crystallization. Various kinds of zeolites having different component ratios, micropore diameters, and specific surface areas are known.

However, it is required that the specific surface area of the zeolite particles used in this invention be at least 150 $m^2/g$ (based on anhydrous zeolite as the standard) and the $SiO_2/Al_2O_3$ mole ratio in the zeolite composition is at most 14, preferably at most 11.

Since a solution of a water-soluble salt of a metal having antibacterial activity used in this invention may easily cause ion exchange with zeolite defined in this invention, the foregoing metal ions can be retained on the solid phase of zeolite by utilizing an ion exchange phenomenon. However, the zeolite particles to retain the metal ion or ions must meet the conditions that the specific area is at least 150 $m^2/g$ and the $SiO_2/Al_2O_3$ mole ratio is at most 14. If the zeolite particles do not meet the foregoing conditions, a desired product having an effective antibacterial activity cannot be obtained, presumably because the absolute amount of the metal ion or ions fixed to zeolite in the state of exhibiting the effect is insufficient. Thus, the effectiveness is considered to depend on physicochemical properties such as the amount of the exchange groups of zeolite, exchange rate, accessibility, etc.

Therefore, zeolite having a larger $SiO_2/Al_2O_3$ mole ratio which is known as a molecular sieve is utterly unsuitable in the present invention.

Also, zeolite having a $SiO_2/Al_2O_3$ mole ratio of at most 14 can uniformly retain the metal ion having antibacterial activity, whereby a sufficient antibacterial activity can first be obtained. Although the acid resistance and alkali resistance of zeolite having a larger $SiO_2/Al_2O_3$ mole ratio over 14 becomes better with the increasing content of $SiO_2$, it takes a long period of time to prepare such zeolite and hence the use of the zeolite having such a high silica content is not beneficial from the economic aspect. Natural or synthetic zeolite having a $SiO_2/Al_2O_3$ mole ratio of at most 14 shows sufficient acid resistance and alkali resitance for ordinary applications of the fiber article and is inexpensive and, therefore, can be advantageously used. From these viewpoints, it is required that the $SiO_2/Al_2O_3$ mole ratio of the zeolite particles be at most 14.

As the zeolite material having a $SiO_2/Al_2O_3$ mole ratio of at most 14 used in this invention, either natural or synthetic zeolite can be used. Examples of natural zeolite to be used in this invention are analcime ($SiO_2/Al_2O_3 = 3.6$ to 5.6), chabazite ($SiO_2/Al_2O_3 = 3.2$ to 6.0 and 6.4 to 7.6), clinoptilolite ($SiO_2/Al_2O_3 = 8.5$ to 10.5), erionite ($SiO_2/Al_2O_3 = 5.8$ to 7.4), faujasite ($SiO_2/Al_2O_3 = 4.2$ to 4.6), mordenite ($SiO_2/Al_2O_3 = 8.34$ to 10.0), phillipsite ($SiO_2/Al_2O_3 = 2.6$ to 4.4). These typical natural zeolites may be preferably used in this invention. Further, typical examples of synthetic zeolite to be used in this invention are A-type zeolite ($SiO_2/Al_2O_3 = 1.4$ to 2.4), X-type zeolite ($SiO_2/Al_2O_3 = 2$ to 3), Y-type zeolite ($SiO_2/Al_2O_3 = 3$ to 6), mordenite ($SiO_2/Al_2O_3 = 9$ to 10). Particularly preferred examples of the zeolites used in this invention are synthetic A-type zeolite, X-type zeolite, Y-type zeolite and synthetic or natural mordenite.

The suitable form of zeolite used in this invention is preferably fine particules. In the case of the fiber material having a large diameter, the particle size may be from several microns to fifty or sixty microns or even above several hundreds microns. In the case of the fiber material having a small diameter, a smaller particle size is preferred, such as 5 microns or less, particularly 2 microns or less.

The metal ions should be retained on the zeolite particles through an ion-exchange reaction. Metal ions which are merely adsorbed or attached without using an ion-exchange reaction show a poor antibacterial effect and an insufficient durability. Two alternative processes enable strong retention of the ions on the zeolite particles.

In the first process, the metal ion is first applied to zeolite, which is then added to a low-melting component of conjugated fibers during or before spun.

In the second process, zeolite is first added to a low-melting component, which is spun into conjugated fibers and, then, the spun fibers are subjected to ion exchange treatment to allow the zeolite in the fibers to retain the metal ion having an antibacterial properties.

First of all, the first process will be described hereinafter in detail. For example, in the case of preparing the Ag-zeolite of this invention using various kinds of zeolites as defined in this invention, an aqueous solution of a water-soluble silver salt such as silver nitrate is usually used for the conversion to the Ag-zeolite and in this case it must be noted that the concentration of the solution is not too high. For example, if the silver ion concentration is too high, e.g. $AgNO_3$ of 1 to 2 molarity (molarity is hereinafter referred to as M), in converting an A-type zeolite or an X-type zeolite (sodium-type zeolite) into an Ag-zeolite by utilizing an ion-exchange reaction, the silver ion in the solution forms silver oxide depositing onto the solid phase of the zeolite as precipitates besides the replacement of sodium ion of the zeolite with silver ion. The precipitation of the silver oxide on the zeolite reduces the porosity of the zeolite, whereby the specific surface area of the zeolite is greatly reduced. Also, even when the reduction of the specific surface area of the zeolite is not so serious, the antibacterial activity of the Ag-zeolite is reduced due to the presence of the silver oxide itself. For preventing the deposition of such excess silver onto the solid phase of zeolite, it is necessary to maintain the concentration of the silver solution in a diluted state, e.g., lower than 0.3M $AgNO_3$, preferably lower than 0.1M $AgNO_3$. With an aqueous $AgNO_3$ solution of such a concentration, the specific surface area of the Ag-zeolite is almost same as that of the original zeolite and the antibacterial function can be utilized at the optimum condition.

In the case of converting the zeolite defined in this invention into a Cu-zeolite, the same phenomenon as mentioned above for the Ag-zeolite will take place depending on a concentration of a solution of a copper salt used for the ion-exchange reaction. For example, when an aqueous solution of 1M $CuSO_4$ is used in converting an A-type or an X-type zeolite (sodium-type zeolite) into a Cu-zeolite by an ion-exchange reaction, $Cu^{2+}$ in the solution is replaced with $Na^+$ of the solid phase of the zeolite but, at the same time, basic precipitates such as $Cu_3(SO_4)(OH)_4$ deposit onto the solid phase of the zeolite, whereby the porosity of the zeolite is reduced and thus the specific surface area thereof is also greatly reduced. For preventing the deposition of the copper onto the solid phase of zeolite, it is preferred to maintain the con-centration of an aqueous solution of a water-soluble copper salt in a diluted state, for example, lower than 0.05M. Using an aqueous $CuSO_4$ solution of such a concentration, the specific surface area of the Cu-zeolite obtained is almost same as that of the original zeolite and the antibacterial function can be utilized at the optimum condition.

As stated above, in the converion of zeolite into Ag-zeolite or Cu-zeolite, there can be deposition of a solid material onto the solid phase of the zeolite depending on the concentration of a salt used for the ion-exchange reaction. However, in the conversion into Zn-zeolite, this does not occur in a concentration of a salt up to about 2 or 3M. Usually, the Zn-zeolite to be used in this invention can be easily obtained using a solution of a zinc salt having a concentration of 2 to 3M.

Alternatively, the deposition of metal compounds detrimental to the antibacterial activity can be prevented by controlling the pH of the metal salt solution below 7 using hydrochloric acid, sulfuric acid or the like as described in Japanese Patent Application Laying-Open No. 181002/1985. With such pH control, the concentration of the metal solution may be higher than these described above, e.g., 0.5M $CuSO_4$.

When the ion-exchange reaction for the conversion into Ag-zeolite, Cu-zeolite or Zn-zeolite is performed batchwise, the zeolite may be immersed in the metal salt solution having the aforesaid concentration. In order to increase the content of the metal in the zeolite, the batch treatment may be repeated. Alternatively, in a column method a desired metal-zeolite is easily obtained by packing the zeolite in an adsorption column and passing the solution of the metal salt having the aforesaid concentration through the column.

The amount of the metal incorporated in the aforesaid metal-zeolite may be less than 30% by weight, preferably 0.001 to 5% by weight in the case of silver, based on anhydrous zeolite. In the case of zinc or copper, the amount of zinc or copper incorporated in the metal zeolite may be less than 35% by weight, preferably 0.01 to 15% by weight, based on anhydrous zeolite. Two or more of silver, copper, zinc and other antibacterial ions may be used together. In this case, the total amount of the antibacterial metal ions may be less than 35% by weight, based on anhydrous zeolite, preferably from about 0.001 to about 15% by weight depending on the composition of metals used.

It should be noted that the amount of the antibacterial metals given to the zeolite must be less than the ion exchange capacity of particular zeolite used, preferably not larger than about 90% of the ion exchange capacity. If this amount exceeds the ion exchange capacity or 90% thereof, the antibacterial effect of such metal-zeolite will drastically decrease as described in the allowed U.S. Ser. No. 008,250, Jan. 29, 1987.

Further, metal ions other than the antibacterial ions, such as sodium, potassium, calcium and so on may remain or co-exist in the metal-zeolite since such ions do not prevent the antibacterial effect.

The antibacterial zeolite particles thus prepared may be incorporated into the low-melting component of conjugated fibers by mixing them with polymer tips which are to be the low-melting component, mixing them with the melted low-melting component to prepare master chips, or mixing them with a monomer. The metal-zeolite may, if desired, be dried before mixed. Drying can suitably be carried out at a temperature of 100° to 500° C. in an atmospheric or a reduced pressure, preferably at 100° to 350° C. in a reduced pressure.

It is preferred that the antibacterial zeolite particles are contained in an amount of 0.05 to 5% by weight, calculated on the low-melting component. If the amount is less than 0.05% by weight, the resultant antibacterial effect is poor. On the other hand, no particular increase of the effect is obtained and physical properties of the fibers are adversely affected with the amount in excess of 5% by weight.

In the second alternative process, zeolite particles containing no antibacterial metal ion are first mixed with a low-melting component, which is then spun into conjugated fibers and thereafter subjected to ion exchange reaction with antibacterial metal ion, where the procedures as described in the first alternative process may be used with the exception that the time when the ion exchange is conducted is different. The zeolite particles which have been mixed in the low-melting component still maintain their capability of the ion exchange. It depends on the nature of a fiber polymer in each case how much zeolite in the fiber can be ion-exchanged. In the case of a relatively highly hydrophilic polymer, since the metal ion penetrates into the deeper part of fibers as water penetrates, the zeolite present in the deeper part of the fibere is also ion-exchanged. Further, even in the case of a hydrophobic polymer, the zeolite present at the surface of fibers is ion-exchanged to a considerable extent.

The bonding strength between the zeolite defined in this invention and the antibacterial metal ion is very high unlike the case where the metal ion is retained onto an adsorptive material such as activated carbon, alumina, etc., simply by a physical adsorption. Therefore, the strong antibacterial performance of the fiber article containing the metal-zeolite and an excellent durability of the antibacterial effect are attained.

The zeolite defined in this invention has the advantage that the reactivity thereof with a metal having antibacterial activity is high. For example, the ion-exchangeable metal ion($Na^+$) in an A-type zeolite, an X-type zeolite, a Y-type zeolite, or chabazite easily undergoes an ion-exchange reaction with $Ag^+$, $Cu^{2+}$, or $Zn^{2+}$ to retain them in the zeolite with a high retaining power. Also, the zeolite defined in this invention has an advantage that the selectivity for the adsorption of the ions such as $Ag^+$, $Cu^{2+}$, or $Zn^{2+}$ is high. This means that even when the fiber article of this invention is used in a liquid or water containing various metal ions, $Ag^+$, $Cu^{2+}$, or $Zn^{2+}$ is stabaly retained in the zeolite and the antibacterial activity of the fiber article can accordingly be maintained for a long period of time.

In addition, the zeolite defined in this invention also has the advantage that its ion-exchange capacity is large and, therefore, a large amount of the metal ion having an antibacterial activity can be retained in the zeolite. Furthermore, the zeolite defined in this invention has the advantage that the amount of the metal ion to be contained in the zeolite particles can be easily controlled in the ion exchange treatment.

The above advantages which are derived solely from the metal-zeolite itself are already disclosed in the aforesaid U.S. Pat. No. 4,525,410.

The fiber material of the present invention may be formed into a desired fiber article and heated above the melting point of the low-melting component. Then, the low-melting component melts and spreads to increase its surface area. Accordingly, a larger amount of the zeolite particles become able to contact with the outer circumstances and, as a result, achieve the higher antibacterial effect and the quicker antibacterial action. To attain a predetermined level of the antibacterial action, the use of a smaller amount of the antibacterial zeolite would be enough in the present invention.

The fiber material of the present invention may be in a drawn or undrawn state and is, typically, staple fibers of 1 to 2 deniers and 1 to 150 mm in cut length. Such staple fibers may suitably be used in producing desired fiber articles such as sanitary materials, ground fabrics, interior materials, floorcloths or carpets, furniture cloths, bedcloths, synthetic tatami mats, disposable diapers, or tissue, wallpaper or wrapping materials manufactured by a wet process of paper making. After formed into a desired shape, optionally together with any other materials, the staple fibers may be heated by hot air, hot steam, infrared rays, or hot plate or roller. The melted low-melting component produces nodes at intersections of the fibers upon cooled to solidify, which nodes function to keep the fiber article as one physically united body. In this sense, the material of the invention is suitable to be used in nonwoven fabric preparation processes.

In addition, since the fiber article according to the invention still has the intrinsic properties of zeolite itself, these properties may be utilized in combination with the antibacterial effects. For instance, combined effects of adsorption and moisture absorption functions of zeolite with the antibacterial action may be utilized. Therefore, a deorizing effect may be attained.

Furthermore, it is also possible to include other functional materials in the fiber article and thereby obtain a combination of the above effects and additional effects of these functional materials. Functional materials to be used include activated carbon for deodorization and adsorption, and silica gel for moisture absorption.

In the prior art process for the production of nonwoven fabrics wherein a resin binder is generally used, if it is tried to produce nonwoven fabrics having antibacterial properties by admixing an antibacterial agent to a fiber polymer or by subjecting fibers to an antibacterial after-processing, the antibacterial effect of the fibers thus obtained is remarkably decreased or completely deprived of due to the binder. In contrast, a hot-welded nonwoven fabrics made from the material of the invention exhibit an excellent antibacterial action without diminishing the intrinsic antibacterial properties of the metal ions.

The invention will further be explained in the following examples. However, these examples should not be construed to limit the invention.

EXAMPLES

The antibacterial zeolite used in the following Examples is commercially available under trade mark Bactekiller A 350 BN from Shinanen New Ceramics Co. This was obtained by ion-exchanging A-type zeolite with 3% by weight of silver ion and 5% by weight of copper ion. The zeolite has an average particle size of 5 to 6 μm, a specific surface area of 500 to 600 m²/g and a $SiO_2/Al_2O_3$ mole ratio of about 2.

EXAMPLE 1

Polyethylene terephthalate (melting point 256° C.) was used as a high-melting component, and polyethylene (melting point 126° C.) as a low-melting component. To the chips of the low-melting component, Bactekiller A 350 BN was admixed in an amount of 2.0% by weight, calculated on the low-melting component. Sheath-core type conjugated fibers were spun at a conjugation ratio of the high-melting component to the low-melting component of 50:50, and drawn to the fineness of 3 deniers/filament and then cut in lengths of 51 mm.

The resultant staple fibers were subjected to carding and formed into a web of 30 g/m², which was put in an oven with a hot air circulation of a temperature of 150° C. for one minute to melt the low-melting component. According to the observation of the resultant nonwoven fabric by a microscope, the low-melting component spread and a lot of zeolite particles were seen on the surface.

EXAMPLE 2

Polyethylene terephthalate (melting point 256° C.) was used as a high-melting component, and polyethylene terephthalate compolymerized with 30% of isophthalic acid was used as a low-melting component. To the chips of the low-melting component, Bactekiller A 350 BN was admixed in an amount of 1.5% by weight, calculated on the low-melting component. Side-by-side type conjugated fibers were spun at a conjugation ratio of the high-melting component to the low-melting component of 50:50, and drawn to the fineness of 2 deniers/filament and then cut in lengths of 51 mm.

The resultant staple fibers were subjected to carding and formed into a web of 150 g/m², which was put in an oven with a hot air circulation of a temperature of 175° C. for two minutes to melt the low-melting component and obtain a nonwoven fabric.

EXAMPLE 3

Polypropylene (melting point 165° C.) was used as a high-melting component, and polyethylene (melting point 126° C.) as a low-melting component. To the chips of the low-melting component, Bactekiller A 350 BN was admixed in an amount of 1.5% by weight, calculated on the low-melting component. Sheath-core type conjugated fibers were spun at a conjugation ratio of the high-melting component to the low-melting component of 50:50, and drawn to the fineness of 2 deniers/filament and then cut in lengths of 51 mm.

The resultant staple fibers were subjected to carding and formed into a web of 30 g/m², which was put in an oven with a hot air circulation of a temperature of 150° C. for one minute to melt the low-melting component and obtain a nonwoven fabric.

COMPARISON EXAMPLE 1

To polymer chips of polyethylene terephthalate as used in Example 1 as the high-melting component, Bactekiller A 350 BN was admixed in an amount of 1.0% by weight, from which filaments of 3 deniers/filament were spun as in Example 1.

COMPARISON EXAMPLE 2

The nonwoven fabric of Example 1 which was not yet heated was the final product of Comparison Example 2.

EVALUATION OF ANTIBACTERIAL EFFECTS

The shake-flask method, Japan Fiber Products Hygienic Processing Association, was used for the evaluation of the antibacterial effect.

In the tests, Staphylococcus aureus IFO 12732 and Escherichia coli IFO 3301 were used as a testing strain.

The extinction rate of the testing strain was culcuated as follows:

$$\text{Extinction rate } (\%) = (A - B)/A \times 100$$

A: number of bacterium in 1 ml of the flask content before shaked.
B: number of bacterium in 1 ml of the flask content after shaked.

The results are as shown in the following table.

| Test | Sample | Extinction Rate | |
| | | S. aureus | E. coli |
| --- | --- | --- | --- |
| 1 | Example 1 | 71.0 | 91.9 |
| 2 | Example 2 | 60.8 | 95.8 |
| 3 | Example 3 | 54.2 | 77.3 |
| 4 | Comparison E. 1 | 12.7 | 16.3 |
| 5 | Comparison E. 2 | 14.5 | 18.2 |

What is claimed is:

1. A process for producing an antibacterial fiber article, said process comprising the steps of:
providing a fiber material comprising conjugated fibers comprising a low-melting component and a high-melting component, said low-melting component occupying at least a part of the periphery of the cross-section of the fibers, said conjugated fibers having mixed therein zeolite particles having a specific surface area of at least 150 m²/g and a $SiO_2/Al_2O_3$ ratio of at most 14, said zeolite particles retaining therein at ion-exchangeable sites of said zeolite at least one metal ion having antibacterial properties;

shaping said fiber material to form a shaped fiber article;

heating said shaped fiber article at a temperature above the melting point of said low-melting component and below the melting point of said high-melting component, whereby said low-melting component spreads to increase its surface area; and cooling said article to a temperature below the melting point of said low-melting component.

2. A process as claimed in claim 1, wherein said high-melting component and said low-melting component are selected from the group of combinations consisting of polyester/polyester; polyester/polyolefin; polyester/polyamide, polyolefin/polyolefin; and polyamide/polyamide.

3. A process as claimed in claim 1, wherein the cross-section of the conjugated fibers is selected from a sheath-core structure composed of a core comprising the high-melting component and a sheath comprising the low-melting component, an incomplete sheath-core structure composed of a core comprising the low-melting component and a sheath comprising the high-melting component with the core being partially exposed at the periphery of the fiber cross-section, and a side-by-side structure in which the low-melting component is placed side-by-side with the high-melting component.

4. A process as claimed in claim 1, wherein the ratio of the area of the high-melting component to the area of the low-melting component in the fiber cross-section is in a range of from 30:70 to 70:30.

5. A process as claimed in claim 1, wherein 0.06 to 5 percent by weight, based on the low-melting component, of the zeolite particles retaining the antibacterial metal ion is retained in the low-melting component.

6. A process as claimed in claim 1, wherein the zeolite particles are composed of A-type zeolite, X-type zeolite, Y-type zeolite, mordenite or a mixture thereof.

7. A process as claimed in claim 1, wherein the metal ion having antibacterial properties is an ion of one or more metals selected from the group consisting of silver, copper, zinc, iron, chromium, nickel, tin and mercury.

8. A process as claimed in claim 7, wherein the metal ion is an ion of one or more metals selected from the group consisting of silver, copper and zinc.

9. A process as claimed in claim 1, wherein the zeolite particles retain therein at least silver ion as the metal ion having the antibacterial properties.

10. A process as claimed in claim 1, wherein the amount of the metal ion having antibacterial properties present on the zeolite particles is less than the ion exchange capacity of the zeolite.

11. A process as claimed in claim 10, wherein the amount of the metal ion having antibacterial properties present on the zeolite particles is about 90% less of the ion exchange capacity of the zeolite.

12. A process according to claim 1, wherein the fiber article is a sanitary material, ground fabric, interior material, floorcloth or carpet, furniture cloth, bedcloth, synthetic tatami mat, facing, disposable diaper, or tissue, wallpaper or wrapping material manufactured by a wet process of paper making.

13. A process as claimed in claim 1, wherein the fiber article is a nonwoven fabric.

* * * * *